United States Patent [19]

Somlo et al.

[11] 4,210,766
[45] Jul. 1, 1980

[54] PROCESS FOR PRODUCING 2-HALO-4-BROMOPHENOLS

[75] Inventors: Tibor Somlo, Birsfelden; Anton Hungerbühler, Basel, both of Switzerland

[73] Assignee: Ciba-Geigy Corporation, Ardsley, N.Y.

[21] Appl. No.: 935,837

[22] Filed: Aug. 22, 1978

[30] Foreign Application Priority Data

Aug. 26, 1977 [CH] Switzerland .................. 10453/77

[51] Int. Cl.² .................. C07C 39/27; C07C 39/28
[52] U.S. Cl. .................. 568/779; 568/774
[58] Field of Search .................. 568/779, 774

[56] References Cited

U.S. PATENT DOCUMENTS

| | | | |
|---|---|---|---|
| 2,452,154 | 10/1948 | Ross | 568/779 |
| 3,449,443 | 6/1969 | Dietzler | 568/779 |

FOREIGN PATENT DOCUMENTS

| | | | |
|---|---|---|---|
| 80139 | 10/1976 | Australia | 568/779 |
| 555267 | 4/1958 | Canada | 568/779 |
| 2144259 | 3/1972 | Fed. Rep. of Germany | 568/779 |
| 2649112 | 5/1977 | Fed. Rep. of Germany | 568/779 |
| 2726436 | 12/1977 | Fed. Rep. of Germany | 568/779 |
| 948601 | 2/1964 | United Kingdom | 568/779 |

OTHER PUBLICATIONS

Anderson, "Chemical Periodicity," pp. 135 and 136, Reinhold Pub. Corp.
Webster, "Inter. Dictionary," 2nd Ed., p. 1194 (homology).
Ratford, et al., "J. Amer. Chemi. Soc.," vol. LV (1933), pp. 2125 to 2131.

*Primary Examiner*—Werren B. Lone
*Attorney, Agent, or Firm*—Harry Falber

[57] ABSTRACT

A process for the production of 2-halo-4-bromophenols of the formula

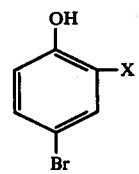

in which X represents chlorine or bromine, is disclosed, which process comprises reacting a brominating agent with a 2-halophenol in the presence of a mixed catalyst consisting of a halide of zinc, iron, aluminium or cobalt, and a diphenyl sulfide of the formula

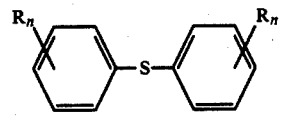

in which R represents methyl or halogen, and n represents 0 to 3.

The new process substantially avoids the formation of undesired 2,6-isomers and the 2-halo-4-bromophenols of the above formula are obtained in excellent yield and purity.

9 Claims, No Drawings

PROCESS FOR PRODUCING 2-HALO-4-BROMOPHENOLS

The present invention relates to a process for producing 2-halo-4-bromophenols of the formula I

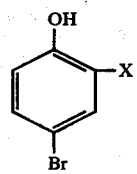

in which X represents chlorine or bromine,
by reacting a brominating agent with a 2-halophenol of the formula II

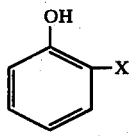

in which X has the meaning given under the formula I.

2-Halo-4-bromophenols of the formula I are valuable intermediates for producing insecticidal and acaricidal active substances. To be mentioned among these are in particular the O-ethyl-S-n-propyl-O-(2-halo-4-bromophenyl)-thiophosphoric acid ester and the O-ethyl-S-n-propyl-O-(2,4-dibromophenyl)-thiophosphoric acid ester, the production and use of which are described in the U.S. Pat. Nos. 3,839,511 and 3,992,533.

It is known that 2-chloro-4-bromophenol can be produced by reacting 2-chlorophenol with bromine at room temperature in carbon tetrachloride. The desired 2-chloro-4-bromophenol is obtained in this manner in a yield of 87% of theory (see CH. Raiford et al., J. Amer. Chem. Soc. 55, 2125 to 2131 (1933)).

Furthermore, it is known from the U.S. Pat. No. 3,449,443 that on reaction of 2-chlorophenol with bromine chloride in carbon tetrachloride at 0° C. there is formed, besides 74% of theory of 2-bromo-6-chlorophenol, only 22% of theory of 2-chloro-4-bromophenol; and at 23° to 26° C. there is formed, besides 61.7% of theory of 2-bromo-6-chlorophenol, only 26.3% of theory of 2-chloro-4-bromophenol.

From the German Offenlegungsschrift No. 2,144,259 is also known the procedure of reacting phenols in the melt, in the presence of brominating catalysts such as iron, aluminium, iron halides, aluminium halides and iodine or mixtures of these substances, with a mixture of bromine and chlorine. This process yields however exclusively highly brominated compounds.

The aforementioned processes are lacking in that above all they are insufficiently selective with regard to the formation of the desired 4-bromophenols. This leads on the one hand to losses in yield, and on the other hand to the necessity of separating the isomers which are always concomitantly formed, especially the 2,6-isomers, since these impair the effectiveness of the final products; and this necessary separating operation constitutes an undesirable additional expenditure.

It is therefore the aim of the present invention to provide a process by which 2-halophenols of the formula II can be brominated in the 4-position more selectively than they can by the processes known hitherto.

It has been found that 2-halo-4-bromophenols are obtained in virtually quantitative yield by brominating a 2-halophenol of the formula II in the presence of a mixed catalyst consisting of a halide of zinc, iron, aluminium or cobalt, and a diphenyl sulfide of the formula III

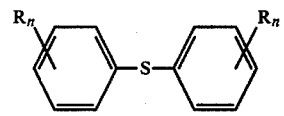

in which
R represents methyl or halogen, and
n represents 0 to 3.

Suitable halides of zinc, iron, aluminium or cobalt are particularly the chlorides and bromides. Zinc halides, in particular zinc chloride, are especially suitable.

As halogen, R in the formula III represents fluorine, chlorine, bromine or iodine, particularly chlorine or bromine. Suitable diphenyl sulfides of the formula III are for example: diphenyl sulfide, 4,4'-dibromodiphenyl sulfide, 4,4'-dimethyldiphenyl sulfide and 2,4,2',4'-tetramethyldiphenyl sulfide. Diphenyl sulfide and 4,4'-dimethyldiphenyl disulfide are especially suitable.

The catalyst mixture according to the invention consists of approximately equimolar amounts of a halide of zinc, iron, aluminium or cobalt and a diphenyl sulfide of the formula III. The applied amounts of catalyst mixture are between 0.1 and 5 percent by weight, preferably between 0.5 and 2 percent by weight, relative to the employed 2-halophenol of the formula II. A catalyst mixture comprising zinc chloride and diphenyl sulfide is particularly preferred.

The process according to the invention can be performed in the presence or absence of an inert solvent. Suitable solvents are for example: sulfur dioxide, or halogenated hydrocarbons such as methylene chloride, chloroform, carbon tetrachloride, 1,2-dichloroethane, tetrachloroethane, chlorobenzene or o-dichlorobenzene. The process according to the invention is preferably performed however in the absence of solvent in the melt.

The process according to the invention is performed at temperatures in the range of 0° to 60° C. The preferred temperature range is between 0° and 30° C. when the process is performed in a solvent. In the case where the process is carried out in the melt, the reaction is performed preferably just above the melting point of the reaction mixture. This means in practice that the bromination in the melt is commenced at a low temperature, and the temperature is successively increased in the course of bromination. In the production of 2-chloro-4-bromophenol by melt bromination, the preferred temperature range is between 0° C. and 55° C., i.e. bromination is started at 0° C., and the temperature is successively raised to 55° C. in the course of bromination.

The bromination according to the invention requires about 1 to 10 hours, depending on the reaction temperature. Advantageous results are obtained if the temperature is selected to ensure that bromination is finished in 3 to 8 hours.

Brominating agents which can be used according to the invention are: elementary bromine, mixtures of chlorine and bromine, bromine chloride, N-bromine compounds such as N-bromosuccinimide, or hypobromites. Elementary bromine is preferred amongst these brominating agents. The brominating agent is used in stoichiometric amounts, or in a slight excess of up to 0.02 mole of bromine per mole of 2-halophenol of the formula II.

The process according to the invention is particularly suitable for producing 2-chloro-4-bromophenol.

It is possible by the process according to the invention to convert 2-halophenols of the formula II, with a practically quantitative conversion and with excellent selectivity, into 4-bromophenols of the formula I. With use of the catalyst mixtures according to the invention, the resulting reaction products contain at most 2% of undesired 2,6-isomer. In the case where catalyst mixtures preferred according to the invention are used, for example a mixture of diphenyl sulfide and zinc chloride, the content of undesired 2,6-isomers can be reduced even to 0.5 percent by weight. The 4-bromophenols of the formula I which can be produced according to the invention are therefore suitable, without further purification, as intermediates for the production of insecticidal phosphoric acid esters, especially O-ethyl-S-n-propyl-O-2-chloro-4-bromophenyl-thiophosphate. Compared with the processes known hitherto, the process according to the invention has the advantage that on the one hand the yield of 4-bromophenol of the formula I is increased, and on the other hand that expensive purifying operations on the intermediates produced are rendered unnecessary.

The process according to the invention is further illustrated by the following Examples.

EXAMPLE 1

321.5 g (2.5 moles) of 2-chlorophenol is placed into a 350 ml sulfonating flask and, with thorough stirring, 400 g (2.5 moles) of bromine is added within 15 hours in a temperature range of 0° to 45° C., the temperature being held continuously just above the crystallisation point of the mixture. The following amounts of bromine are added at the specified bromination temperatures:

| 0° C. | 100 g of bromine | 30° C. | 40 g of bromine |
|---|---|---|---|
| 10° C. | 80 g of bromine | 40° C. | 80 g of bromine |
| 20° C. | 60 g of bromine | 45° C. | 40 g of bromine |
| | | total: | 400 g of bromine |

After completion of the bromine addition, stirring is maintained for 30 minutes at 50° C. The reaction product is subsequently freed at 60° C. under reduced pressure from the dissolved hydrogen bromide to yield 514.6 g (99.15% of theory) of chlorobromophenol which, according to gas-chromatographical determination, has the following composition:

| 2-chlorophenol | 0.12 % by weight |
|---|---|
| 2-chloro-6-bromophenol | 6.60 % by weight |
| 2-chloro-4-bromophenol | 93.14 % by weight |
| 2-chloro-4,6-dibromophenol | 0.14 % by weight |

EXAMPLE 2

326.4 g (2.04 moles) of bromine is added dropwise, within 6 hours, to a mixture of 257.2 g (2 moles) of 2-chlorophenol, 2.0 g of zinc chloride and 2.0 g of diphenyl sulfide, the reaction temperature being held continuously just above the crystallisation point of the mixture. The following amounts of bromine are added at the individual reaction temperatures:

| 0° C. | 100 | g of bromine |
|---|---|---|
| 10° C. | 40 | g of bromine |
| 20° C. | 40 | g of bromine |
| 30° C. | 60 | g of bromine |
| 40° C. | 60 | g of bromine |
| 45° C. | 46.4 | g of bromine |
| total: | 326.4 | g of bromine |

After the total amount of bromine has been added, the mixture is stirred for 30 minutes at 50° C., and is then freed at 60° C. under a pressure of 18 Torr from dissolved hydrogen bromide to yield 414.2 g (99.7% of theory) of chlorobromophenol which, according to gas-chromatographical determination, has the following composition:

| 2-chlorophenol | 0.85 % by weight |
|---|---|
| 2-chloro-6-bromophenol | 0.52 % by weight |
| 2-chloro-4-bromophenol | 98.63 % by weight |

EXAMPLE 3

326.4 g (2.04 moles) of bromine is added dropwise in the course of 6 hours with vigorous stirring, within a temperature range of between 20° and 45° C., to a mixture of 257.2 g (2 moles) of 2-chlorophenol, 1.0 g of zinc chloride and 1.0 g of diphenyl sulfide. After the addition of 70 ml of bromine, the temperature rises to 35° C. To avoid crystallisation, the reaction mixture is afterwards heated to 40° C. and a further 20 ml of bromine is added dropwise. The remaining bromine is finally added at 45° C. After the addition of bromine is complete, stirring is maintained for 30 minutes at 50° C., and subsequently the reaction product is freed at 60° C. under reduced pressure from dissolved hydrogen bromide to leave 414.5 g (99.8% of theory) of chlorobromophenol which, according to gas-chromatographical analysis, has the following composition:

| 2-chlorophenol | 1.10 % by weight |
|---|---|
| 2-chloro-6-bromophenol | 1.05 % by weight |
| 2-chloro-4-bromophenol | 97.85 % by weight |

EXAMPLE 4

313 g of a mixture of bromine and bromine chloride, which consists of 88.95% by weight of bromine and 11.05% by weight of bromine chloride, is added dropwise in the course of 6 hours with vigorous stirring, within a temperature range of between 0° and 45° C., to a mixture of 257.2 g (2 moles) of 2-chlorophenol, 1.0 g of zinc chloride and 1.0 g of diphenyl sulfide, the temperature of the mixture during this time being held just above the crystallisation point. The following amounts of the mixture of bromine and bromine chloride are added at the specified reaction temperatures:

| 0° C. | 90 | g of $Br_2$/BrCl |
|---|---|---|
| 10° C. | 40 | g of $Br_2$/BrCl |
| 20° C. | 40 | g of $Br_2$/BrCl |
| 30° C. | 40 | g of $Br_2$/BrCl |
| 40° C. | 60 | g of $Br_2$/BrCl |

-continued

| 45° C. | 43 g of Br₂/BrCl |

After completed addition of the mixture of bromine and bromine chloride, the reaction mixture is stirred for 30 minutes at 50° C., and is subsequently degassed at 60° C. under a pressure of 18 Torr to yield 413.0 g (99.4% of theory) of chlorobromophenol which, according to gas-chromatographical analysis, has the following composition:

| 2-chlorophenol | 0.05 % by weight |
| 2-chloro-6-bromophenol | 1.15 % by weight |
| 2-chloro-4-bromophenol | 98.35 % by weight |

EXAMPLE 5

257 g (2 moles) of 2-chlorophenol is brominated, in the manner described in Example 1, with the use of a variety of catalyst mixtures. Chlorobromophenol is thus obtained in yields of 99.5 to 99.8% of theory. Further experimental data regarding the catalyst mixtures used and the composition of the final products obtained are given in the following Table:

| Catalyst mixture | Yield % of theory | Product composition | |
|---|---|---|---|
| | | % by weight of 2-chloro-6-bromophenol | % by weight of 2-chloro-6-bromophenol |
| 3.7 g of 4,4'-dibromodiphenyl sulfide + 1.4 g of zinc chloride | 99.7 | 97.8 | 1.5 |
| 2.5 g of 4,4'-dimethylphenyl sulfide + 2.0 g of zinc chloride | 99.5 | 99.2 | 0.6 |
| 3.0 g of 2,4,2',4'-tetramethyldiphenyl sulfide + 2.0 g of zinc chloride | 99.8 | 98.5 | 1.0 |

EXAMPLE 6

257.2 g (2 moles) of 2-chlorophenol is reacted, in the presence of various catalyst mixtures consisting of 2.0 g of phenyl sulfide and 0.01 mole of metal salt, with 313 g (1.96 moles; 102 ml) of bromine. The first 80 ml of bromine is added at a rate of 0.4 ml per minute, and the remaining 22 ml of bromine at a rate of 0.2 ml per minute. The addition is made in the temperature range of between 0° C. and 45° C. The following amounts of bromine are added at the specified reaction temperatures:

| 0° C. | 32 | ml of bromine |
| 10° C. | 16 | ml of bromine |
| 20° C. | 8 | ml of bromine |
| 30° C. | 16 | ml of bromine |
| 40° C. | 16 | ml of bromine |
| 45° C. | 14 | ml of bromine |
| total: | 102 | ml of bromine |

After all the bromine has been added, the reaction mixture is stirred at 50° C. for a further ½ hour, and is subsequently degassed at 60° C. under a pressure of 18 Torr. In the individual tests are obtained amounts of 413.0 to 414.5 g (99.5 to 99.8% of theory) of chlorobromophenol. Further experimental data regarding the type and amount of the metal salt used and the composition of the final product obtained are given in the Table which follows.

| Metal halide | Amount g | Yield % of theory | Product composition | |
|---|---|---|---|---|
| | | | % by weight of 2-bromo-2-chlorophenol | % by weight of 6-bromo-2-chlorophenol |
| aluminium chloride | 1.33 | 99.5 | 96.8 | 2.0 |
| cobalt (II) chloride-hexahydrate | 2.38 | 99.5 | 98.2 | 1.5 |
| iron (II) chloride tetrahydrate | 1.90 | 99.8 | 98.4 | 1.45 |
| iron (III) chloride hexahydrate | 2.70 | 99.7 | 97.8 | 1.95 |
| zinc chloride | 1.37 | 99.6 | 99.2 | 0.48 |

EXAMPLE 7

Bromination with bromine chloride

To produce a solution of bromine chloride in carbon tetrachloride, 71.0 g (1 mole) of chlorine is introduced at 0° to 1° C. during 1 hour into a solution of 160 g (1 mole) of bromine in 400 ml of carbon tetrachloride. The resulting solution of bromine chloride is then added dropwise at 23° to 26° C. in the course of 2.8 hours, with stirring, to a solution of 257.2 g (2 moles) of 2-chlorophenol, 4 g of zinc chloride and 2 g of diphenyl sulfide. After completion of the addition of bromine chloride, the reaction mixture is stirred for a further 30 minutes, and subsequently left to stand overnight. The reaction mixture is then washed five times with 300 ml of water each time, and processed by distillation. The type and the amount of final products obtained are given in the following Table. There are shown in this Table, for the purpose of comparison, also the results obtained by the process according to Example 1 of the U.S. Pat. No. 3,449,443.

| Product | Process according to present invention | | Process according to U.S. Pat. Specification No. 3,449,443 | |
|---|---|---|---|---|
| | Amount g | Yield % of theory | Amount g | Yield % of theory |
| 2-chlorophenol | 3.3 | 1.3 | 19.3 | 7.5 |
| 2-chloro-6-bromophenol | 33.2 | 8.0 | 283.2 | 74.0 |
| 2-chloro-4-bromophenol | 365.0 | 88.0 | 84.6 | 22.0 |
| dibromophenol | 1.5 | 0.2 | 11.3 | 2.0 |

EXAMPLE 8

128 g (0.8 mole) of bromine is added dropwise, within 6 hours, to a mixture of 138.4 g (0.8 mole) of 2-bromophenol, 0.8 g of zinc chloride and 0.8 g of diphenyl sulfide, the reaction temperature being held during this time continuously just above the crystallisation point of the mixture. The following amounts of bromine are added at the specified reaction temperatures:

| 0° C. | 65 | g of bromine |
| 20° C. | 40 | g of bromine |
| 40° C. | 24 | g of bromine |

-continued

| total: | 128 | g of bromine |

After completed addition, the mixture is stirred for 30 minutes at 50° C., and is subsequently freed at 60° C. under a pressure of 18 Torr from dissolved hydrogen bromide. The yield obtained is 200 g (99.2% of theory) of dibromophenol which, according to gas-chromatographic analysis, has the following composition:

| 2-bromophenol | 0.42 % by weight |
| 2,6-dibromophenol | 2.01 % by weight |
| 2,4-dibromophenol | 97.28 % by weight |

We claim:

1. A process for producing 2-halo-4-bromophenols of the formula I

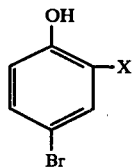
(I)

in which X represents chlorine or bromine, by bromination of 2-halophenols of the formula II

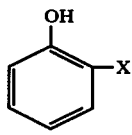
(II), in which X has the meaning given under the formula I, which process comprises brominating, at a temperature of from about 0°–60° C., a halophenol of the formula II in the presence of from about 0.1–5.0%, by weight of said 2-halophenol, of a mixed catalyst consisting of approximately equimolar amounts of a halide of zinc, iron, aluminum or cobalt, and a diphenyl sulfide of the formula III

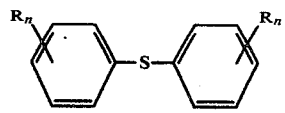
(III)

in which
R represents methyl or halogen, and
n represents 0 to 3;
said bromination utilizing a bromination agent selected from the group consisting of elementary bromine, mixtures of chlorine and bromine, bromine chloride, N-bromine compounds and hypobromites.

2. A process according to claim 1, wherein the employed halides of zinc, iron, aluminum or cobalt are the chlorides or bromides.

3. A process according to claim 1, wherein the employed diphenyl sulfide of the formula III is diphenyl sulfide, 4,4'-dibromodiphenyl sulfide, 4,4'-dimethyldiphenyl sulfide or 2,4,2',4'-tetramethyldiphenyl sulfide.

4. A process according to claim 1, wherein diphenyl sulfide is used.

5. A process according to claim 1, wherein there is used, relative to the employed amount of 2-halophenol of the formula II, 0.5 to 2 percent by weight of a catalyst mixture consisting of approximately equimolar amounts of a halide of zinc, iron, aluminium or cobalt, and a diphenyl sulfide of the formula III.

6. A process according to claim 1, wherein there is used, relative to the employed amount of 2-halophenol of the formula II, 0.5 to 2 percent by weight of a catalyst mixture consisting of approximately equimolar amounts of zinc chloride and diphenyl sulfide.

7. A process according to claim 1, wherein bromination of the 2-halophenol of the formula II is performed in the presence of an inert solvent in the temperature range of between 0° and 30° C.

8. A process according to claim 1, wherein bromination of the 2-halophenol of the formula II is performed in the absence of a solvent at a temperature which in each case is just above the melting temperature of the reaction mixture.

9. The process according to claim 1, wherein said brominating agent is elementary bromine.

* * * * *